United States Patent
Akihiro

(10) Patent No.: US 10,098,719 B1
(45) Date of Patent: Oct. 16, 2018

(54) PERIODONTAL POCKET PROBING DEVICE

(71) Applicant: Actwell Technology Inc., Taipei (TW)

(72) Inventor: Yoshiaki Akihiro, Taipei (TW)

(73) Assignee: Actwell Technology Inc., Taipei (TW)

( * ) Notice: Subject to any disclaimer, the term of this patent is extended or adjusted under 35 U.S.C. 154(b) by 0 days.

(21) Appl. No.: 15/604,608

(22) Filed: May 24, 2017

(51) Int. Cl.
*A61C 19/04* (2006.01)

(52) U.S. Cl.
CPC .................................. *A61C 19/043* (2013.01)

(58) Field of Classification Search
CPC .................................................... A61C 19/043
See application file for complete search history.

(56) References Cited

U.S. PATENT DOCUMENTS

| | | | | |
|---|---|---|---|---|
| 4,364,730 A * | 12/1982 | Axelsson | ................. | A61C 5/42 433/141 |
| 5,090,902 A * | 2/1992 | Lemon | ................. | A61C 19/043 33/514 |
| 5,676,544 A * | 10/1997 | Urban | ....................... | A61C 3/00 433/147 |
| 6,024,564 A * | 2/2000 | Kesling | ................ | A61C 19/043 433/141 |
| 6,409,505 B1 * | 6/2002 | Kesling | ................ | A61C 19/043 433/141 |
| 2012/0231411 A1 * | 9/2012 | Verronneau | .............. | A61C 3/00 433/75 |

\* cited by examiner

*Primary Examiner* — Ralph Lewis

(57) ABSTRACT

A periodontal pocket probing device facilitating fabrication and application and effectively reducing the cost is disclosed to include a main body, and a probe having a connection portion located at one end thereof and connected to the main body and a flat probing tip located at an opposite end thereof and defining a flat front end edge on a front side thereof opposite to the connection portion for allowing the produced pressure to be distributed in all directions to reduce the patient's pain upon insertion of the probe into the deep inside of a periodontal pocket.

9 Claims, 12 Drawing Sheets

A-A

PERIODONTAL POCKET PROBING DEVICE

BACKGROUND OF THE INVENTION

1. Field of the Invention

The present invention relates to periodontal proving technology and more particularly, to a periodontal pocket probing device with an improved design of probe.

2. Description of the Related Art

At present, evaluating a periodontal disease is to insert a periodontal pocket probing device into a deep inside of a periodontal pocket for probing. The probe of a known periodontal pocket probing device is shaped like a needle. In evaluation, the probe is inserted into the periodontal pocket to measure the depth of the periodontal pocket by reading the graduations on the probe. During the evaluation, the probe will repeatedly pierce the gum tissue, resulting in unbearable pain and fear. There is another design of periodontal pocket probing device that has an elastic member loaded on the probe for allowing the probe to be moved out of the gum tissue when the pressure encountered by the probe surpasses a predetermined level. Although the probe can be moved away from the gum tissue when it encounters a pressure greater than the predetermined level, however the probe has stung the patient before it is moved away from the gun tissue. Further, this design of periodontal pocket probing device has a complicated structure, and its manufacturing cost is high.

SUMMARY OF THE INVENTION

The present invention has been accomplished under the circumstances in view. It is therefore the main object of the present invention to provide a periodontal pocket probing device, which facilitates fabrication to reduce the cost and can reduce the patient's pain during periodontal pocket evaluation.

To achieve this and other objects of the present invention, a periodontal pocket probing device comprises a main body and a probe. The probe comprises a connection portion located at one end thereof and connected to the main body, and a flat probing tip located at an opposite end thereof and defining a flat front end edge on a front side thereof opposite to the connection portion for allowing the produced pressure to be distributed in all directions to reduce the patient's pain upon insertion of the probe into the deep inside of a periodontal pocket.

Preferably, the periodontal pocket probing device further comprises a probe assembly and a control rod set respectively connected to the main body. The probe assembly comprises a probe control rod, and a probe adapter connected to the probe control rod and adapted to hold the probe. The probe control rod is mounted in the main body. The probe adapter is disposed outside the main body. The control rod set comprises a flanged control rod, and a baffle connected to the flanged control rod. The flanged control rod is pivotally mounted in the main body. The baffle is disposed outside the main body, comprising a contact member located at a distal end thereof to surround the probe in such a manner that when the contact member is stopped by an object and the flanged control rod is biased by a user, the probe is extended out of the contact member.

DETAILED DESCRIPTION OF THE PREFERRED EMBODIMENT

Figure 1:
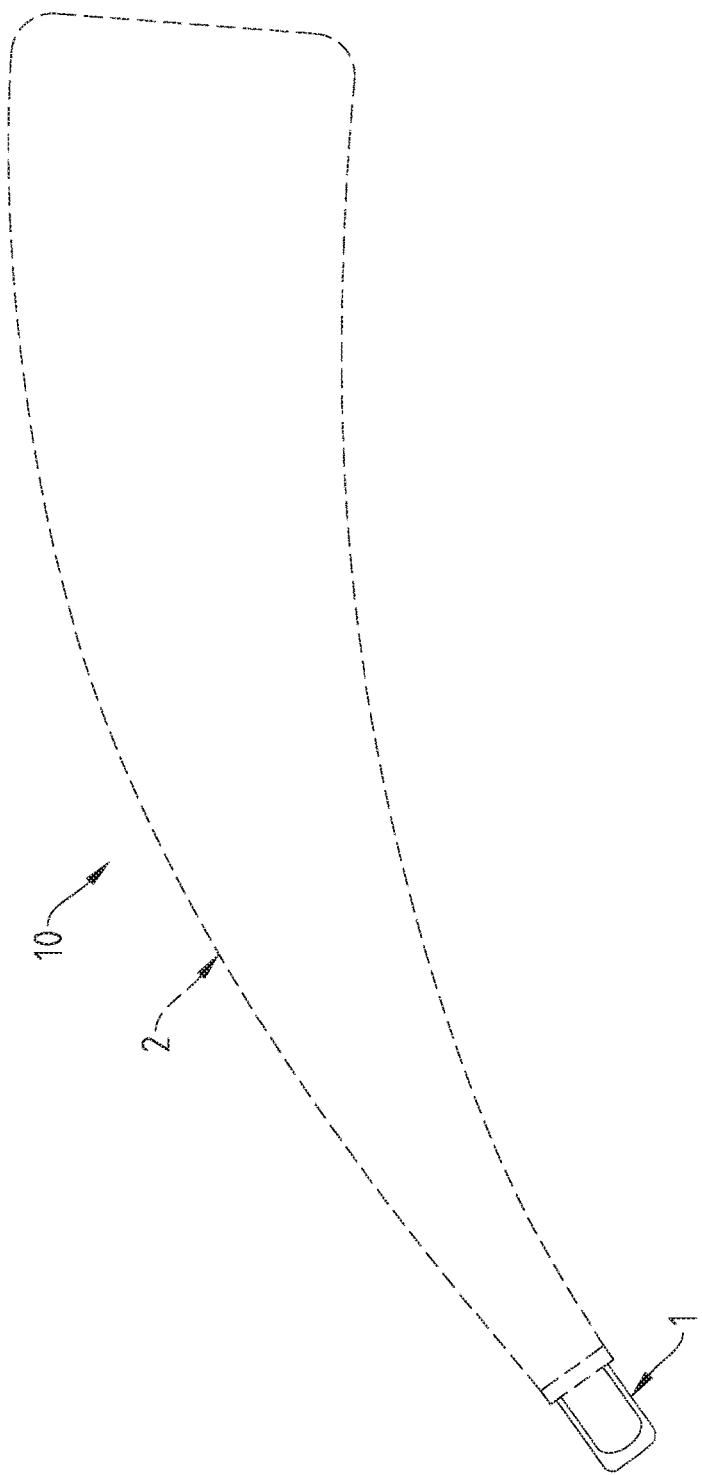
FIG. 1 is a schematic drawing illustrating a periodontal pocket probing device in accordance with a first embodiment of the present invention.
Figure 2:
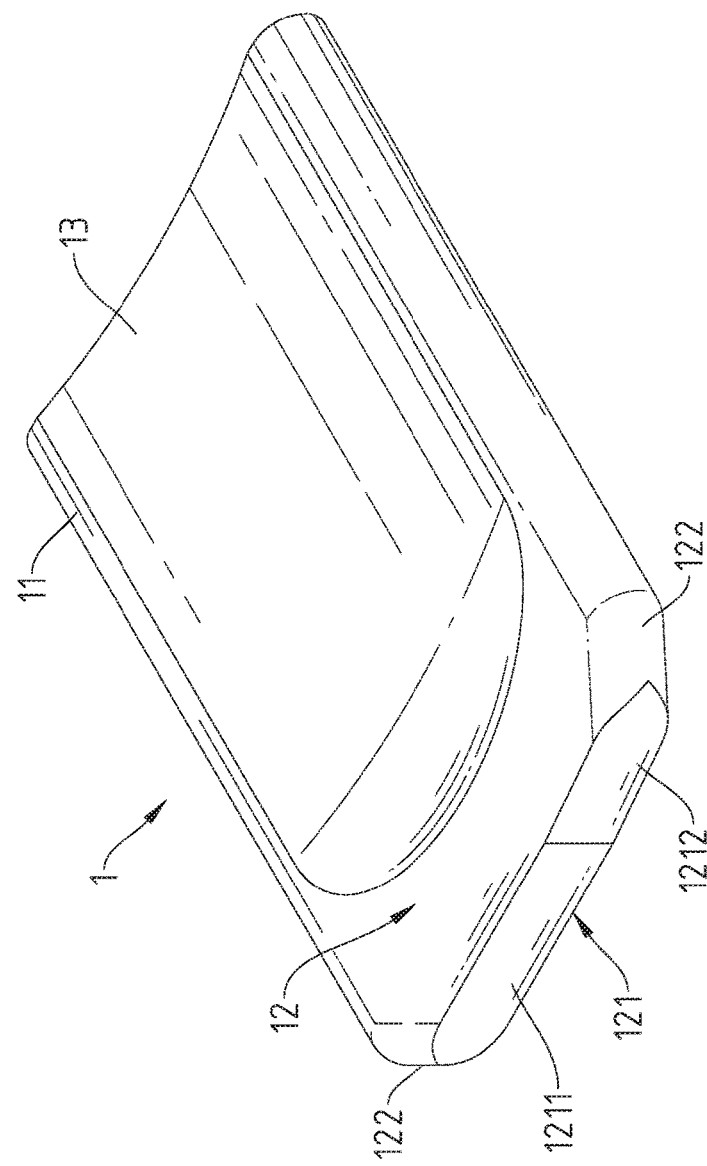
FIG. 2 is an elevational view of the probe of the periodontal pocket probing device in accordance with the first embodiment of the present invention.
Figure 3:
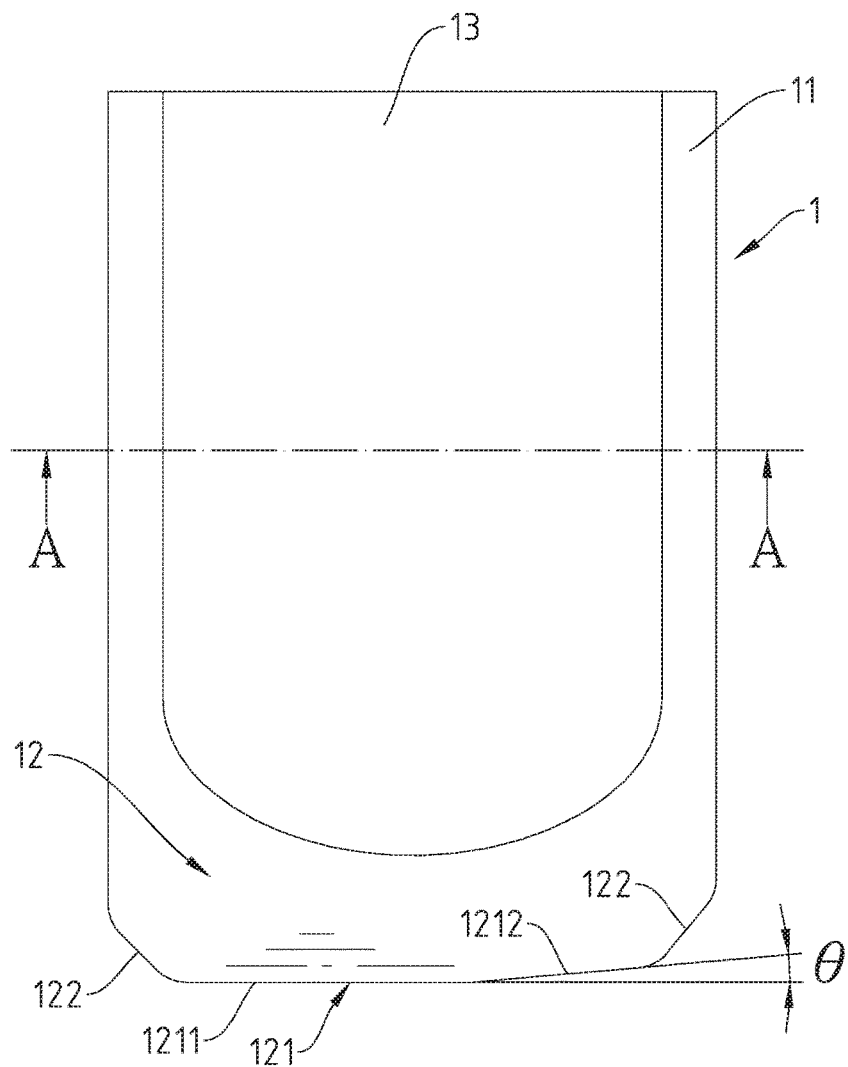
FIG. 3 is a top view of the probe of the periodontal pocket probing device in accordance with the first embodiment of the present invention.
Figure 4:
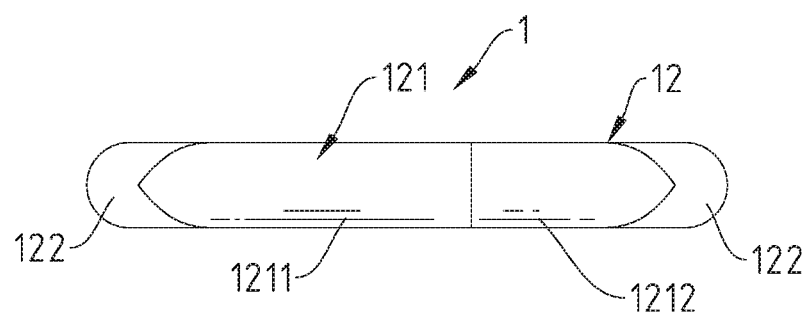
FIG. 4 is a front view of the probe of the periodontal pocket probing device in accordance with the first embodiment of the present invention.
Figure 5:
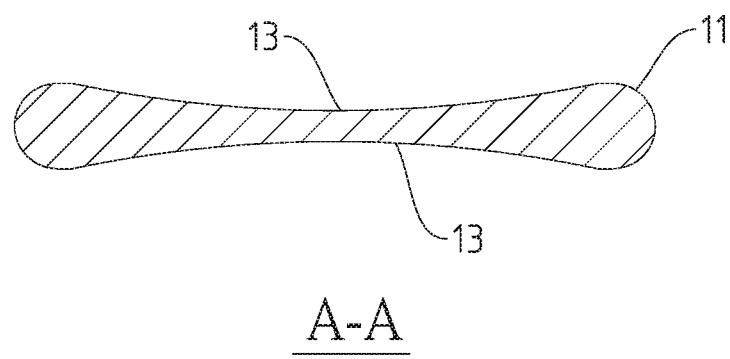
FIG. 5 is a sectional view taken along line A-A of FIG. 3.

Referring to FIGS. 1-5, a periodontal pocket probing device 10 in accordance with a first embodiment of the present invention is shown. The periodontal pocket probing device 10 comprises a main body 2, and a flat probe 1 connected to one side of the main body 2. The probe 1 comprises a connection portion 11 located at a rear side thereof and connected to the main body 2, a probing tip 12 located at an opposing front side thereof, and two recessed surfaces 13 respectively defined on opposing top and bottom sides of the connection portion 11. The recessed surfaces 13 are arc shaped. The probing tip 12 defines a flat front end edge 121 on a front side thereof opposite to the connection portion 11, and two beveled guide edges 122 respectively extended from two opposite lateral sides of the flat front end edge 121 in direction toward the connection portion 11. Further, the beveled guide edges 122 have a width gradually increased in direction from the flat front end edge 121 toward the connection portion 11. Thus, each beveled guide edge 122 has two opposite ends thereof respectively connected to the flat front end edge 121 and the connection portion 11. Further, the beveled guide edges 122 respectively extend from the periphery of the probing tip 12 to opposing top and bottom surfaces thereof in a smoothly arched manner. Further, the flat front end edge 121 of the probe 1 defines a contact area 1211, and an inclined area 1212 extended from one lateral side of the contact area 1211. The contact area 1211 is disposed in a perpendicular relationship with the connection portion 11. The inclined area 1212 extends obliquely from the contact area 1211 toward the connection portion 11, and thus, the contact area 1211 and the inclined area 1212 define therebetween a contained angle θ.

Figure 6:
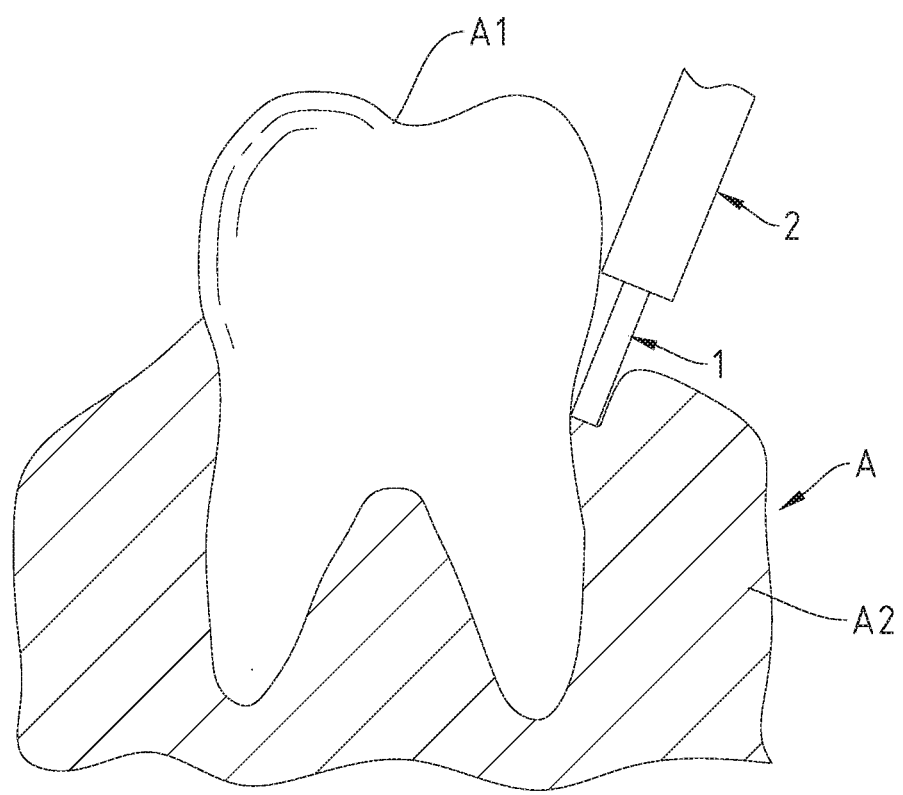
FIG. 6 is a schematic drawing illustrating an application status of the periodontal pocket probing device in accordance with the first embodiment of the present invention.

Referring to FIG. 6 and FIGS. 1-5 again, when using the periodontal pocket probing device, insert the probing tip 12 of the probe 1 into the periodontal pocket A between the tooth A1 and the gum tissue A2. Since the probing tip 12 is flat shaped, the pressure applied by the probing tip 12 to the gum tissue A2 is distributed in different directions, reducing the pain generated during the periodontal pocket evaluation. Subject to the planar design of the flat front end edge 121 of the probing tip 12, a surface contact can be created between the flat front end edge 121 and the gum tissue A2, the pressure being applied to the gum tissue A2 can be minimized during the periodontal pocket evaluation, and the gum tissue A2 can be pushed to the recessed surface 13, lowering the pressure to squeeze the gum tissue A2 and reducing the pain.

Further, since the beveled guide edges 122 of the probing tip 12 respectively extend from the periphery of the probing tip 12 to the opposing top and bottom surfaces of the probing tip 12 in a smoothly arched manner, the pressure produced upon contact between the flat front end edge 121 and beveled guide edges 122 of the probing tip 12 and the gum tissue A2 during the periodontal pocket evaluation can be minimized, reducing the pain.

When performing a normal periodontal pocket evaluation, the contact area 1211 of the flat front end edge 121 is forced into contact with the gum tissue A2; in the evaluation of the periodontal pocket A around the big molar of the upper jaw, in order to avoid touching the big molar of the upper jaw or the alveolar bone of the big molar, the probe 1 must be tilted, allowing the inclined area 1212 of the flat front end edge 121 to touch the gum tissue A2; similarly, since the contact area 1211 and inclined area 1212 of the flat front end edge 121 are planar, either the contact area 1211 or the inclined area 1212 is forced into contact with the gum tissue A2, a surface contact is created, effectively reducing the pain.

Figure 7:
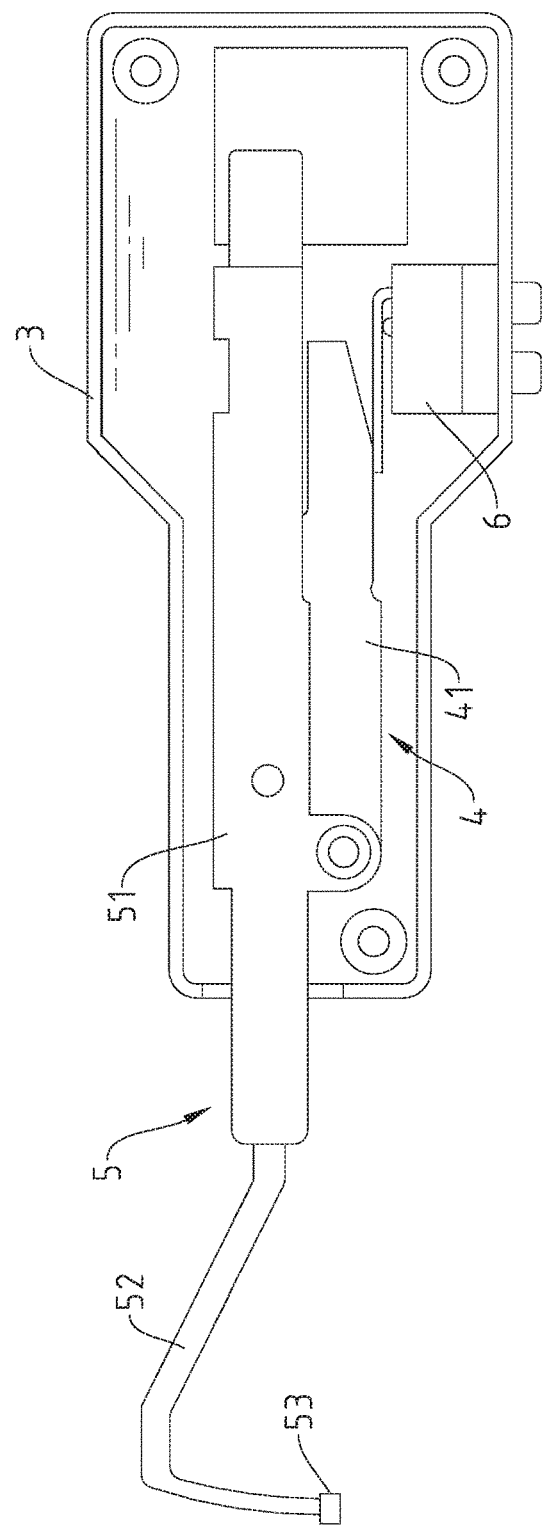
FIG. 7 is a schematic plain view a periodontal pocket probing device in accordance with a second embodiment of the present invention.
Figure 8:
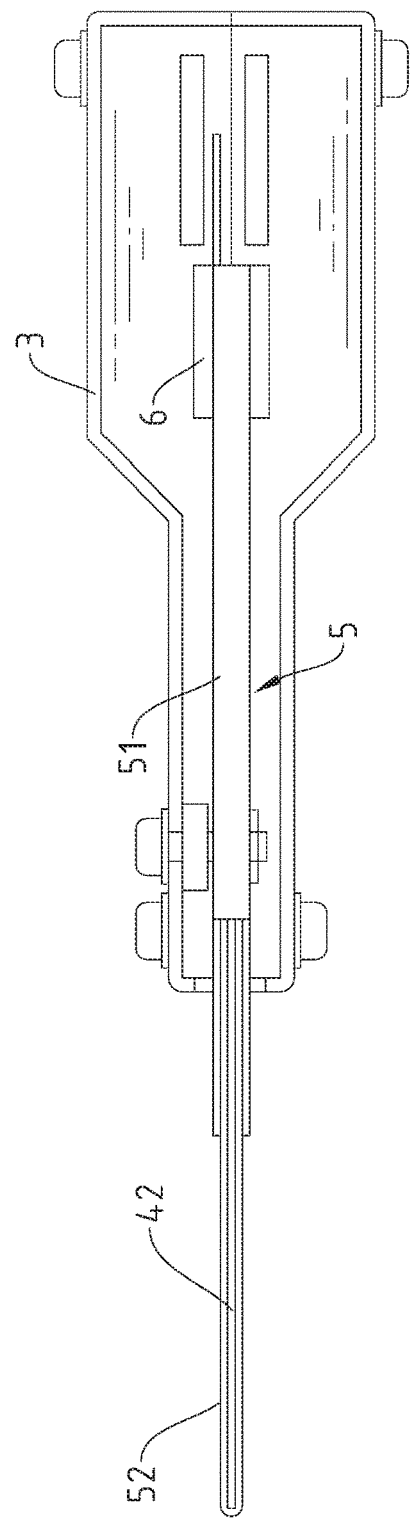
FIG. 8 corresponds to FIG. 7 when viewed from another angle.
Figure 9:
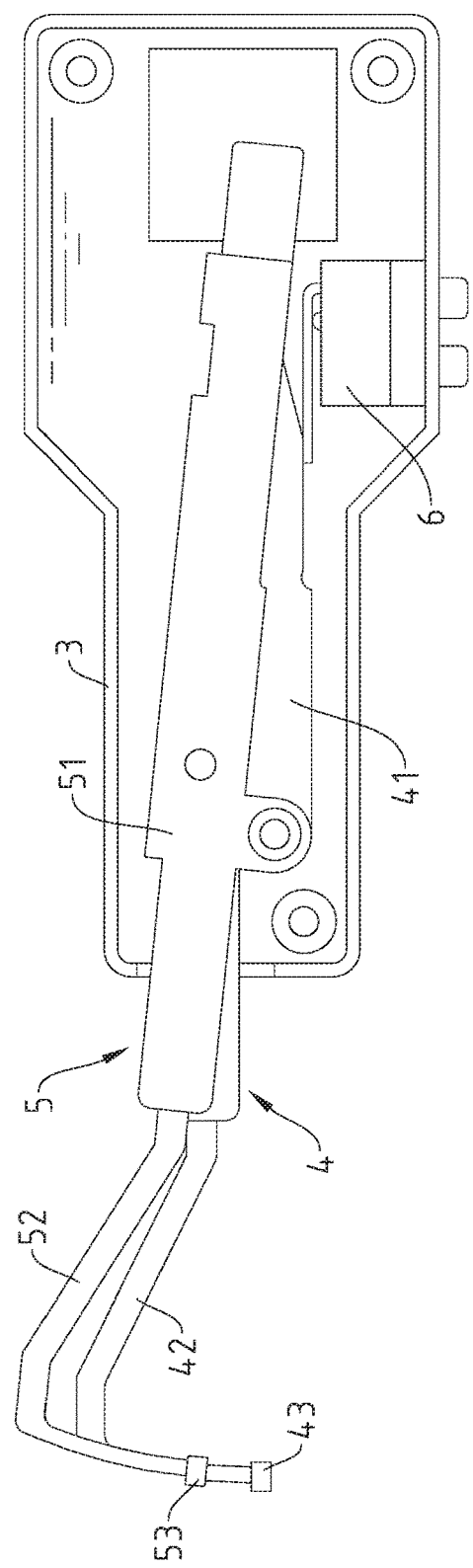
FIG. 9 corresponds to FIG. 8, illustrating the probe extended out of the contact member.

Referring to FIGS. 7-9, a periodontal pocket probing device in accordance with a second embodiment of the present invention is shown. The periodontal pocket probing device of this second embodiment comprises a main body 3, a probe assembly 4 and a control rod set 5. The probe assembly 4 comprises a probe control rod 41 pivotally mounted in the main body 3, a probe adapter 42 connected to the probe control rod 41 and disposed outside the main body 3, and a probe 43 detachably connected to the probe adapter 42. The probe 43 is same as the probe 1 of the aforesaid first embodiment. The control rod set 5 comprises a flanged control rod 51 pivotally mounted in the main body 3, a baffle 52 connected to the flanged control rod 51 and disposed outside the main body 3, and a contact member 53 detachably connected to a distal end of the baffle 52. The probe 43 is disposed in the contact member 53. Further, a switch 6 is mounted in the main body 3 at one lateral side relative to a rear end of the probe control rod 41.

Figure 10:
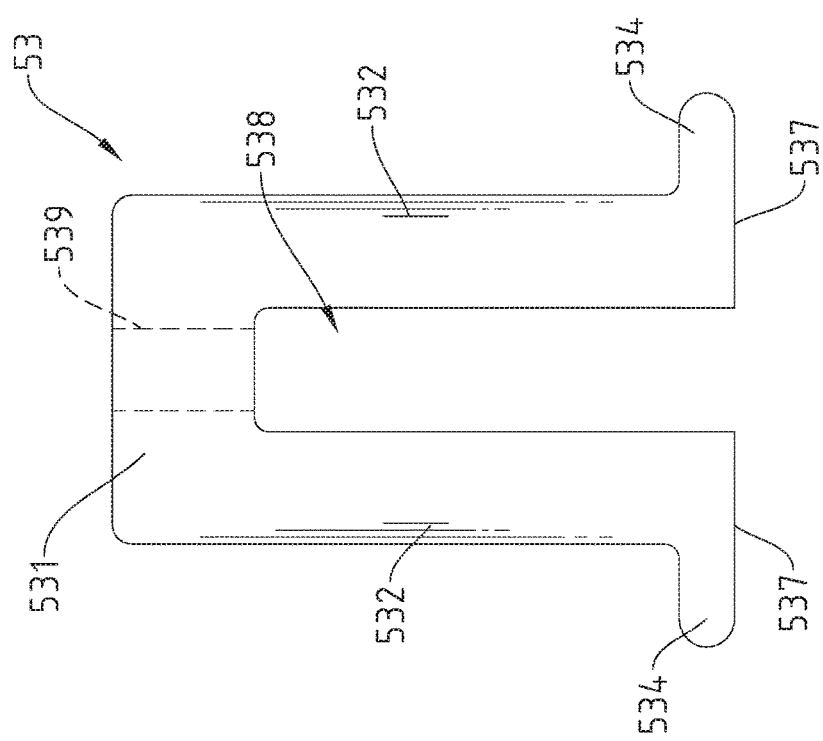
FIG. 10 is a front view of the contact member of the periodontal pocket probing device in accordance with the second embodiment of the present invention.
Figure 11:
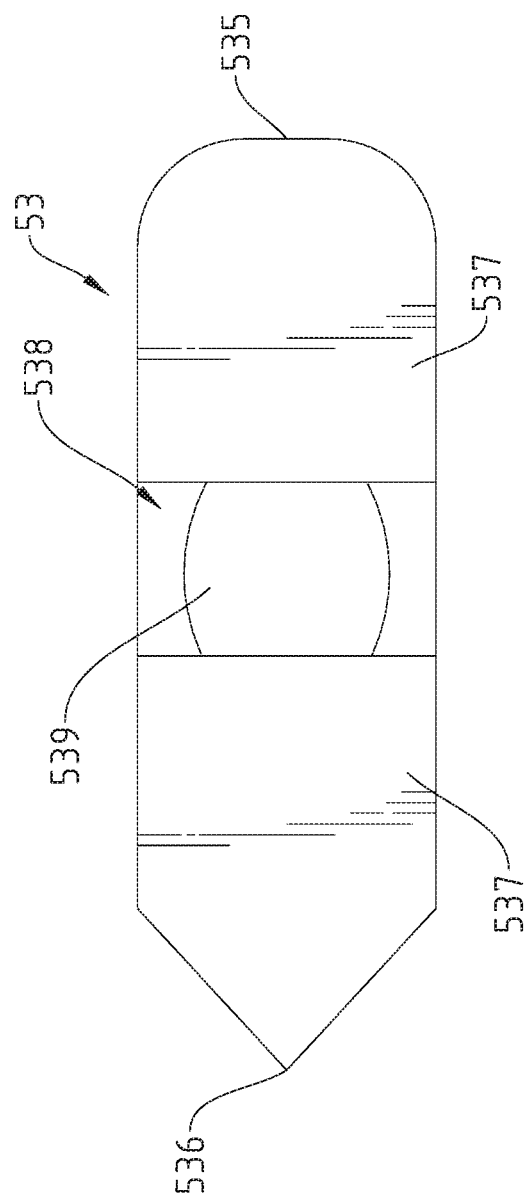
FIG. 11 is a bottom view of the contact member of the periodontal pocket probing device in accordance with the second embodiment of the present invention.
Figure 12:
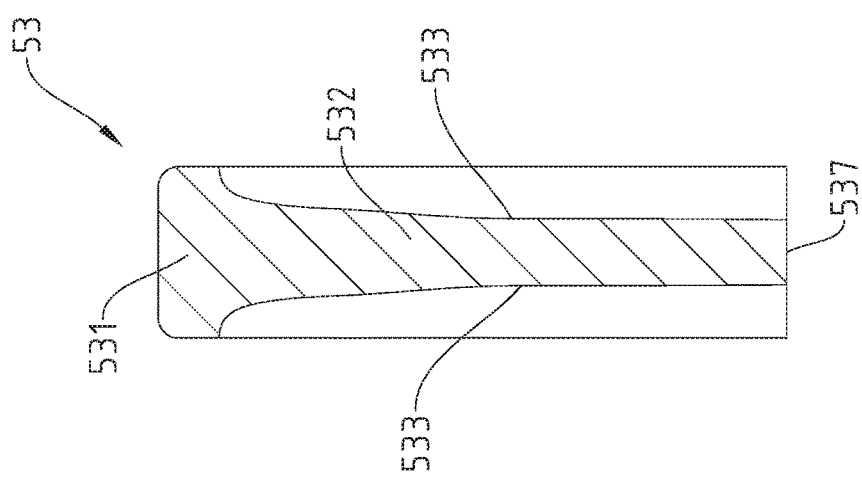
FIG. 12 is a sectional view of the contact member of the periodontal pocket probing device in accordance with the second embodiment of the present invention.

Referring to FIGS. 10-12, the contact member 53 comprises a base portion 531, two opposite sidewalls 532 bilaterally extended from the base portion 531, two smoothly curved recessed surface portions 533 respectively defined on the two opposite sidewalls 532 at an outer side, two protruding flanges 534 respectively transversely extended from respective distal ends of the two opposite sidewalls 532 in reversed directions and terminating in a rounded surface portion 535 or tapered tip 536 (alternatively, the two protruding flanges 534 can be respectively terminating in a tapered tip, or a rounded surface portion, a planar contact surface portion 537 defined on a bottom side of each sidewall 532 opposite to the base portion 531, an accommodation gap accommodation gap 538 defined between the two opposite sidewall 532 for accommodating the probe 43, and a through hole 539 cut through the base portion 531 in communication with the accommodation gap 538 for the passing of the probe 43.

Referring to FIGS. 7-12, in application of this second embodiment, insert the contact member 53 into the periodontal pocket to be examined. When inserting the contact member 53 into the periodontal pocket, the planar contact surface portions 537 of the contact member 53 firstly touch the gun tissue and are prohibited from entering the periodontal pocket, allowing the probe 43 to be exposed to the outside of the contact member 53 and inserted into the inside of the periodontal pocket. At this time, the tapered tip 536 of the contact member 53 can be easily inserted in between the two adjacent teeth, allowing the probe 43 to access to the inside of the periodontal pocket. Since the tooth or the gum tissue can be squeezed toward the smoothly curved recessed surface portion 533 of the contact member 53, the probe adapter 42 and the baffle 52 can easily be tilted, allowing the probe 43 to be inserted to the deep inside of the periodontal pocket. Further, when the probe 43 encounters a resistance upon its insertion into the periodontal pocket, the probe control rod 41 can be biased and abutted against the switch 6 to switch on the evaluation.

Further, since the probe 43 is detachably connected to the probe adapter 42 and the contact member 53 is detachably connected to the baffle 52, the probe 43 and the contact member 53 can be detached for sterilization, facilitating the application.

What is claimed is:

1. A periodontal pocket probing device, comprising:
   a main body;
   a probe having a connection portion located at one end thereof and connected to said main body, and a probing tip located at an opposite end thereof for probing;
   wherein said probing tip is a flat tip, defining a flat front end edge on a front side thereof opposite to said connection portion;
   the periodontal pocket probing device further comprising:
   a probe assembly and a control rod set respectively connected to said main body,
   said probe assembly comprising a probe control rod and a probe adapter connected to said probe control rod and adapted to hold said probe,
   said probe control rod being mounted in said main body,
   said probe adapter being disposed outside said main body,
   said control rod set comprising a flanged control rod and a baffle connected to said flanged control rod,
   said flanged control rod being pivotally mounted in said main body, said baffle being disposed outside said main body and baffle comprising a contact member located at a distal end thereof to surround said probe in such a manner that when said contact member is stopped by an object and said flanged control rod is biased by a user, said probe is extended out of said contact member.

2. The periodontal pocket probing device as claimed in claim 1, wherein:
   said connection portion of said probe is flat-shaped; and
   said probe further comprises two recessed surfaces respectively defined on opposing top and bottom sides of said connection portion, said recessed surfaces being arc shaped.

3. The periodontal pocket probing device as claimed in claim 1, wherein said probing tip defines a flat front end edge on a front side thereof opposite to said connection portion, and two beveled guide edges respectively extend from two opposite lateral sides of said flat front end edge in a direction toward said connection portion.

4. The periodontal pocket probing device as claimed in claim 3, wherein said two beveled guide edges of said probe respectively extend from a periphery of said probing tip to opposing top and bottom surfaces thereof in a smoothly arched manner.

5. The periodontal pocket probing device as claimed in claim 1, wherein said flat front end edge of said probe defines a contact area, and an inclined area extends from one lateral side of said contact area, said contact area being disposed in a perpendicular relationship with said connection portion, said inclined area extending obliquely from said contact area toward said connection portion.

6. The periodontal pocket probing device as claimed in claim 1, wherein said contact member comprises:
 a base portion,
 two opposite sidewalls bilaterally extended from said base portion, and
 two smoothly curved recessed surface portions respectively defined on said two opposite sidewalls at an outer side.

7. The periodontal pocket probing device as claimed in claim 1, wherein said contact member comprises:
 a base portion,
 two opposite sidewalls bilaterally extended from said base portion, and
 two protruding flanges respectively transversely extended from respective distal ends of said two opposite sidewalls in reversed directions, one said protruding flange having a distal end thereof terminating in a rounded surface portion, the other said protruding flange having a distal end thereof terminating in a tapered tip.

8. The periodontal pocket probing device as claimed in claim 1, wherein said contact member comprises:
 a base portion,
 two opposite sidewalls bilaterally extended from said base portion, and
 a planar contact surface portion defined on a distal end of each said sidewall.

9. The periodontal pocket probing device as claimed in claim 1, wherein said contact member comprises:
 a base portion,
 two opposite sidewalls bilaterally extended from said base portion, an accommodation gap defined between said two opposite sidewalls for accommodating said probe, and
 a through hole cut through said base portion for the passing of said probe.

* * * * *